United States Patent [19]

Mocilac et al.

[11] 4,429,960
[45] Feb. 7, 1984

[54] KERATOMETRIC DEVICE

[76] Inventors: Joseph P. Mocilac, 11785 Telephone Ave., Chino, Calif. 91710; Clifford M. Terry, 7087 Columbus Dr., Anaheim, Calif. 92807; John G. Mesaros, 18142 Hallsworth Cir., Villa Park, Calif. 92667

[21] Appl. No.: 202,458

[22] Filed: Oct. 31, 1980

[51] Int. Cl.³ .............................................. A61B 3/10
[52] U.S. Cl. ................................................... 351/212
[58] Field of Search ...................... 351/6, 13, 16, 212, 351/221; 128/22, 745, 303.1

[56] References Cited

U.S. PATENT DOCUMENTS

| | | | |
|---|---|---|---|
| 1,523,528 | 1/1925 | Henker | 351/13 X |
| 3,183,519 | 5/1965 | Harris et al. | 351/13 X |
| 3,542,458 | 3/1968 | Volk | 351/13 X |
| 3,969,019 | 7/1976 | Nohda | 351/13 |
| 4,046,463 | 9/1977 | LaRussa | 351/13 |
| 4,157,859 | 6/1979 | Terry | 350/35 |
| 4,165,744 | 8/1979 | Cravy | 351/13 |
| 4,315,672 | 2/1982 | Müller | 351/13 |
| 4,375,320 | 3/1983 | Smirmaul | 351/212 |

*Primary Examiner*—F. L. Evans
*Attorney, Agent, or Firm*—John G. Mesaros

[57] ABSTRACT

A keratometric device for attachment to a surgical microscope, the device including a housing member configured for receiving the bottom portion of the microscope therein, a screw elevator member rotatable relative to the housing member, having a screw thread about the exterior thereof and a second screw thread about the interior thereof. A ring gear is affixed to the elevator member with a knob and gear arrangement provided for rotating the elevator member. A ring lamp is provided with roller bearings engaging the external screw thread, the ring lamp providing a reference image. A prism support member is provided with outwardly extending roller bearing members for engaging the internal screw thread with a prism tray slidably movable relative to the prism support. A prism assembly is affixed to the prism tray for pivotal movement through a predetermined angle. The prism assembly includes a pair of disc-shaped prisms of different diameters mounted one atop the other for intercepting and deviating light passing through to the objective lens of the microscope for creating two virtual images in addition to the reference image. An electronic circuit provides a digital display indicative of the composite position of the ring lamp and prism support.

17 Claims, 8 Drawing Figures

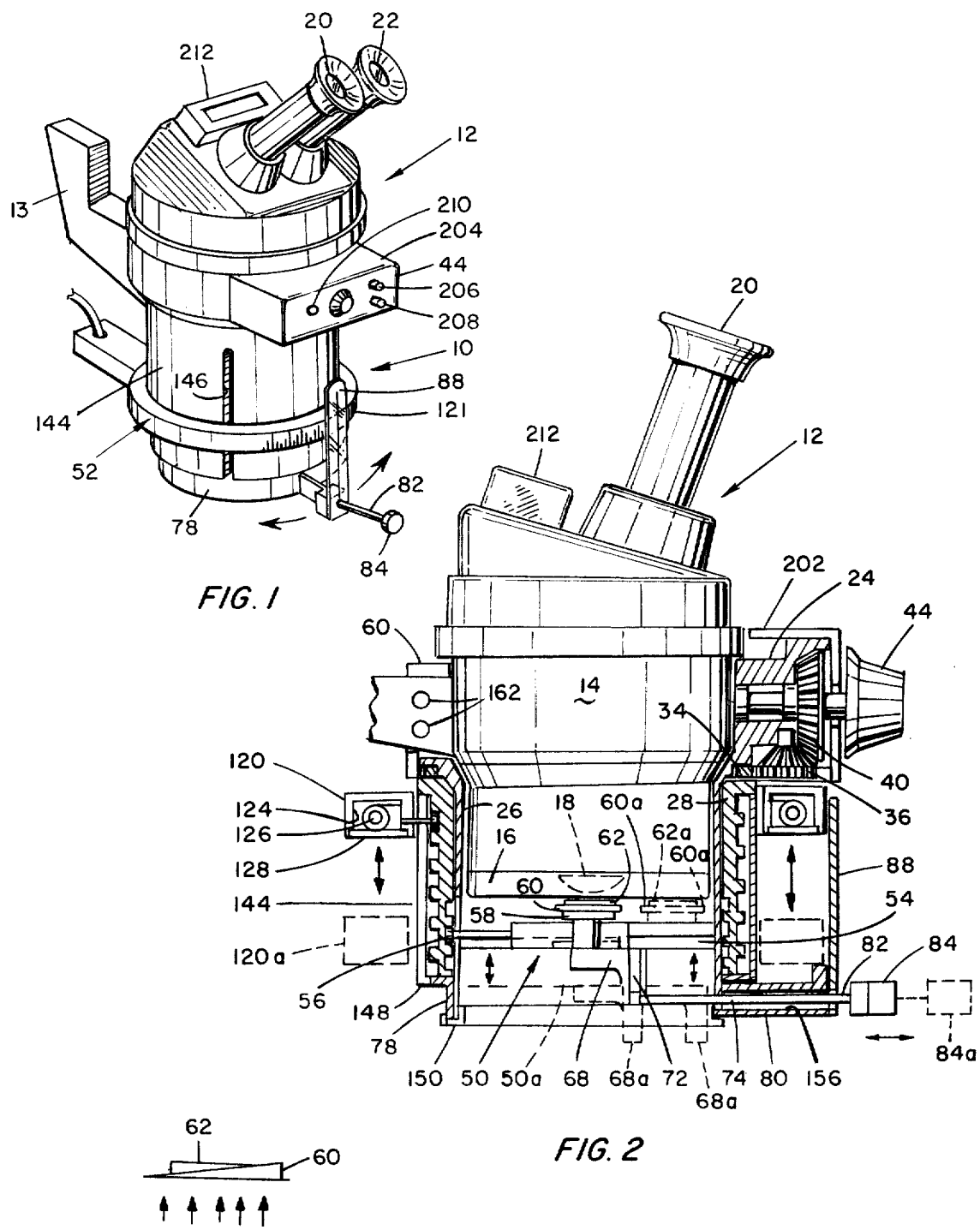

{ 4,429,960 }

KERATOMETRIC DEVICE

BACKGROUND OF THE INVENTION

The background of the invention will be discussed in two parts:

1. Field of the Invention

This invention relates to a keratometric device, and more particularly to a keratometric device for attachment to a binocular surgical microscope for use in observing and measuring the spherical surface of a cornea.

2. Description of the Prior Art

During ophthalmic surgery, for example surgery involving cataracts, ideally it is desirable to reconfigure the cornea after the operation to the same radius of curvature existing prior to the operation. In the human eye, the radius of curvature vaaries from individual to individual with a normal range being between forty and fifty diopters which correspond to radii of curvature of 8.44 millimeters to 6.75 millimeters respectively. In order to ascertain the radius of curvature prior to the operation, the surgeon would normally take measurements, in the office, along certain angles or meridians. Such prior art measurement techniques involve the use of telescopic instruments known as ophthalmometers or Keratometers. This information relating to the radius of curvature of the cornea will then become a part of the patient's history file. The operation would then be performed and on the next office visit after the operation, the patient's eye would then be remeasured to determine what effect the operation had on the radius of curvature.

A corneal measurement technique is shown and described in U.S. Pat. No. 3,895,860 and a keratometer device is referred to in U.S. Pat. No. 3,972,602.

U.S. Pat. No. 4,157,859 issued June 12, 1979 to Clifford Terry for a "Surgical Microscope System." The microscope system of this patent depicts an advanced system and method for enabling a surgeon to observe the changes of radius of curvature during suturing of the incision required for cataract operations. With this system, a binocular microscope is employed, the microscope having means for projecting an image onto the cornea, the image preferably being a circle created by a ring lamp surrounding the microscope body adjacent the objective lens. A pair of prisms are mounted on a slidable tray member for partially intercepting each of the two light paths through the microscope, the prism powers being selected for creating two virtual images in a predetermined relation to each other and to the real image.

In measuring the radius of curvature of the cornea, the zoom mechanism is adjusted until the two formed images viewable through the microscope are in tangential relation with the real image with the zoom power being proportional to the radius of curvature provided on a display in diopters of power. A complete discussion of the principles and operation, as well as structure of the surgical microscope system of U.S. Pat. No. 4,157,859 may be had by reference thereto, that description being fully incorporated herein by this reference.

In the microscope system of U.S. Pat. No. 4,157,859, the prisms for creating the formed images are placed into the optical path immediately below the binocular assembly and above the zoom mechanism. This particular construction was facilitated by virtue of the construction of the Zeiss OPMI6 microscope which has a detachable eyepiece assembly with the body being con- Other surgical microscopes utilized by ophthalmic surgeons, however, are not modularly configured, and the utilization of the system of that patent in such other microscopes would require reconstruction of major parts of the microscope.

It is accordingly an object of this invention to provide a new and improved keratometric device.

It is another object of this invention to provide a new and improved keratometric device for use with a binocular surgical microscope.

It is a further object of this invention to provide a new and improved keratometric device which may be simply and economically fitted to existing surgical microscopes.

SUMMARY OF THE INVENTIQN

The foregoing and other objects of the invention are accomplished by providing a new and improved keratometric device having a main housing member configured for at least partially encircling the body of the microscope adjacent the objective lens thereof. The housing member includes a cylindrical shell portion receiving thereon a rotatable screw elevator member, the elevator member having an external thread and an internal thread. A ring gear is coupled to the screw elevator member with a knob and gear mechanism enabling the operator to rotate the screw elevator member. A ring lamp for providing a reference image coacts with the external screw thread while a prism support member coacts with the internal screw thrad. Roller bearing members engaging the external screw thread have shaft members affixed to the inner periphery of the ring lamp. Similarly, roller bearing members engaging the inner screw thread have the shafts thereof secured to the prism suppbrt member.

The shaft members of the roller bearing members of the prism support member extend through slots in the cylindrical shell portion of the housing member for preventing rotation of the prism support during raising or lowering thereof upon rotation of the elevator member. Similarly, an outer sleeve is provided for encircling the outer periphery of the screw member with the outer sleeve having axially extending slots for passage therethrough of the shafts of the roller bearing members of the ring lamp.

A pair of disc-shaped prisms are coaxially mounted one atop the other to a pivotable prism assembly. The prism assembly is mounted on a prism tray slidable radially relative to the prism support. The two prisms are of different diameter aligned relative to each other to provide formed images in mutually perpendicular directions with the power of the prisms selected for deviating the reference image the same distance in each direction.

The outer periphery of the ring lamp is provided with a protractor scale with the prism assembly being provided with a handle including a scribe indicator for measuring the angle of pivoting of the prism assembly.

Electronic circuitry is provided for receiving a signal from a potentiometer coupled to the ring gear to provide a numerical indication to a display device of the radius of curvature.

In operation, the prism support and ring lamp move in the same direction relative to the objective lens of the microscope with the electronic circuitry being calibrated to indicate the composite movement as a radius of curvature.

Further objects, features and advantages of the invention will become apparent upon a reading of the specification when taken in conjunction with the drawings in which like reference numerals refer to like elements in the several views.

BRIEF DESCRIPTION OF THE DRAWINGS

FIG. 1 is a perspective view illustrating the keratometric device according to the invention mounted on a binocular microscope;

FIG. 2 is a side elevational view depicting the surgical microscope with the keratometric device thereabout, the device being in cross-sectional view with dotted lines illustrating the movement of the various parts;

FIG. 4 is a side elevational view of the prism assembly utilized in the device of FIG. 1;

DESCRIPTION OF THE PREFERRED EMBODIMENT

Figure 3:
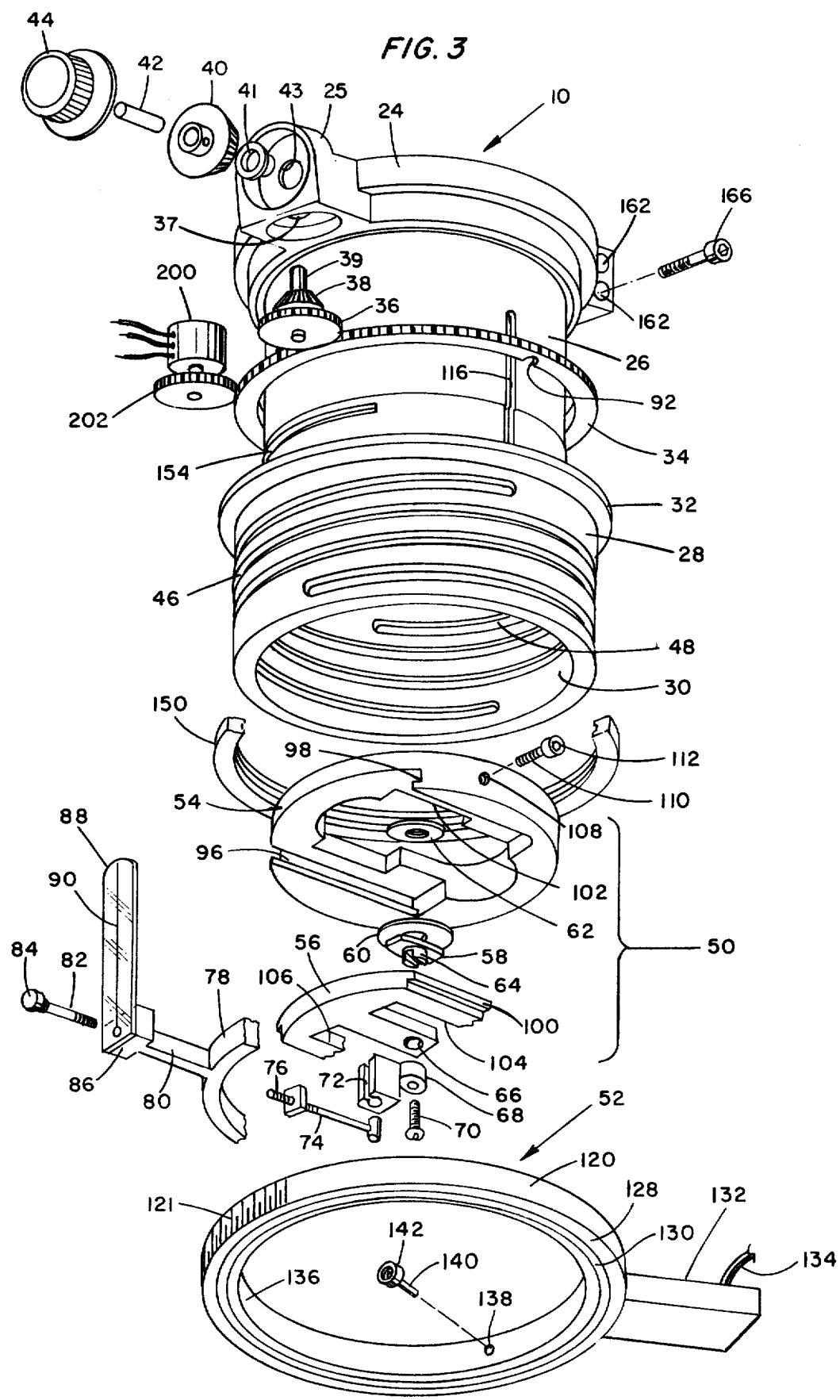
FIG. 3 is an exploded perspective view of the operative components of the keratometric device shown in FIG. 1.

Referring now to the drawings and more particularly to FIG. 1 there is shown a keratometric device generally designated 10 assembled on the bottom portion of a binocular surgical microscope generally designated 12. Such surgical microscopes are fitted with an objective lens at the lower end thereof, such objective lenses being designated by the "working distance," such as 150 mm or 175 mm. These designations ordinarily refer to the distance between the objective lens and the cornea with the microscope in focus, this distance being referred to as the "working distance." Normal working distances are 150 mm to 200 mm for ophthalmic surgery.

By reference to FIG. 2, the binocular microscope 12 is provided with a circular body portion 14 terminating at the lower end thereof with an objective lens mount 16, the lens mount 16 supporting an objective lens 18 (shown in dotted lines). In some microscope systems, there may be one objective lens 18 covering both optical paths, or conversely there may be one objective lens 18 for each optical path. At the upper portion of the microscope 12, there are two eyepieces 20 and 22 for permitting binocular viewing by the surgeon.

In accordance with the present invention, the body 14 of the microscope 12 is surrounded by a housing member 24 having an interior configuration matingly engaging the body 14 of the microscope 12. The body 14 is circular in cross-section with the inner diameter of the housing member 24 closely corresponding thereto. The housing member 24 is provided with a downwardly depending integral cylindrical shell portion 26 which serves as the main support for the movable components of the keratometric device 10.

Referring also to FIG. 3, an elevator member 28 has an opening 30 of a diameter slightly greater than the outer diameter of the cylindrical shell 26 for rotation relative thereto. The elevator member 28 is provided with a peripheral outwardly extending flange portion 32 which receives thereon in fixed relation a ring gear 34. The ring gear 34 has the outer periphery thereof engaging a gear member 36 which includes a bevel gear portion 38 for coacting with a second bevel gear 40 fitted to a shaft 42 and knob assembly 44 within the enlarged upper portion of the housing member 24. Rotation of the knob 44 rotates the ring gear 34 along with the elevator member 32.

The elevator member 28 is provided with a screw thread 46 about the outer surface thereof and is further provided with a second screw thread 48 on the inner periphery thereof with the inner screw thread 48 having a smaller pitch than the outer screw thread 46.

The inner screw thread 48 provides means for moving, in an axial direction, a prism slide assembly generally designated 50 (within the bracket as illustrated in FIG. 3) while the outer screw 46 provides for axial movement of a ring lamp assembly generally designated 52. Both the prism slide assembly and ring lamp assembly 52 move in the same direction at the same time in proportional relation as the elevator 28 is rotated by means of the knob 44 and the gear train coupled to the ring gear 34.

The prism slide assembly 50 includes a prism support 54 having a circular cross-section of slightly smaller diameter than the internal diameter of the cylindrical shell portion 26 of the housing member 24 for fitting therein. The prism slide assembly also includes a prism tray 56 configured for receiving thereon a prism mount 58 and first and second prisms 60 and 62. The prism mount 58 includes a shaft portion 64 extending through an aperture 66 in one leg of the prism tray 56, the shaft portion 64 engaging a pivotal coupling member 68 to which it is fastened by suitable means such as a screw 70 for concurrent pivoting. The coupling member 68 is provided with an axially extending keyhole slot 72 for receiving therein the matingly configured end of an actuating rod 74. The actuating rod 74 is provided with a threaded end 76. For enabling pivoting, a collar member 78 encircles the lower end of the cylindrical shell portion 26 of the housing member 24, the collar member 78 having an arm portion 80 extending radially outwardly therefrom, the arm portion 80 having an aperture extending therethrough for enabling the threaded end 76 of the actuating rod 74 to be inserted therethrough for threadably receiving an extender rod 82 having a knob 84 at the end thereof for gripping by the operator. A block member 86 is provided at the end of arm 80 with an index pointer member 88 secured to the outer surface thereof and extending in an axial direction with a centrally disposed scribe line 90 thereon.

By reference to FIGS. 2 and 3, the device is assembled as follows. The ring gear 34 is positioned on the flange 32 of the elevator member 28 and pinned or indexed thereto for concurrent movement. One means of affixation may be one or more detents 92 on ring gear 34 configured and positioned for mating engagement with pins (not shown) extending upwardly from the flange 32.

The shaft 39 of the gear member 36 is then positioned within aperture 37 of the enlarged boss portion 25 of the housing member 24 with the gear 40, bushing 41, shaft 42 and knob 44 being in assembled relation and inserted into the aperture 43 of the enlarged boss portion 25.

With the parts thus assembled, rotation of knob 44 will rotate ring gear 34 along with elevator member 32.

The prism slide assembly 52 is then assembled. The prisms 60 and 62 are glued to each other in predetermined orientation and secured to the prism mount 58. The shaft 64 is then inserted through aperture 66 and keyed relative to the enlarged boss portion of coupling member 68 with the screw 70 then being inserted and the parts secured together in lined relation with each other. The dimensioning of shaft 64 is sufficient to enable rotation or pivoting thereof within the aperture 66 of the prism tray 56. The prism tray 56 is then assembled to the prism support 54 and for this purpose, the prism support 54 is provided with parallel opposing guideways 96 and 98 for slidably receiving therein the matingly configured guide edges 100 of the prism tray 56. As illustrated in FIG. 3, the prism support 54 is provided with an irregularly configured opening 102, the opening 102 being configured to permit the passage of light or images through the objective lens of the microscope 12 as well as providing cutouts for illumination sources with the microscope. Similarly, the prism tray 56 is provided with knockouts 104 and 106 for enabling the passage of light with the keratometric device 10 assembled to the microscope 12.

After assembly of the parts of the prism tray 56, the tray 56 slides into the prism support 54. The periphery of the prism support member 54 is provided with three apertures 108 (only one of which is shown), the aperture 108 being radially extending for receiving a shaft 110 supporting a roller bearing member 112 at the other end thereof.

The prism assembly 50 is then inserted into the open end of the cylindrical shell 26 of the housing member 24 with each of the shafts 110 associated with a roller bearing 112 passing through axially extending slots 116 formed in the cylindrical shell 26. Although only one slot 116 is shown, it is to be understood that there are at least three such slots 116 for suitably supporting the prism assembly 50. Each of the roller bearings 112 engages the screw thread 48 formed on the interior of the elevator member 28. Thus, as the elevator member 28 rotates, the prism slide assembly 50 will be displaced vertically or axially relative to the longitudinal center line of the cylindrical shell 26 with the slots 116 coacting with the shafts 110 serving as a guide to prevent rotation of the prism support 54 during vertical movement thereof.

With the prism slide assembly 50 thus positioned at the bottom of the thread 48, the ring lamp assembly 52 is then mounted. Ring lamp assembly 52 includes a ring lamp housing 120 of a generally toroidal configuration with an opening 124 therein for receiving the ring lamp source 126 (see FIG. 2) with the open end of the opening 124 being covered by a window 128 which is suitably masked to provide only a fine line 130 of circular configuration for providing a reference image on the cornea when the lamp 126 is energized. The lamp 126 is formed of tubular stock with electrical connections thereto passing through a handle portion 132 of the housing 120 with an electrical cord 134 for connecting to a suitable source of power. The inner surface 136 of the housing 120 is of a diameter slightly larger than the outer diameter of the elevator member 28, the surface 136 being provided with equiangularly disposed radially extending apertures 138 for receiving therein shaft members 140 supporting roller bearing members 142 at the other ends thereof. Although only one such roller bearing member 142 is illustrated in FIG. 3, it is to be understood that there are three of such roller bearings equiangularly disposed about the inner periphery of surface 136. The roller bearing members 142 are configured for being received within the outer screw thread 46 of the elevator member 28 for enabling vertical or axial movement of the ring lamp assembly 52 upon rotation of the screw member 28. With the ring lamp assembly 52 and the prism slide assembly 50 thus mounted, rotation of the elevator member 28 will simultaneously move both assemblies in the same direction in proportion determined by the pitches of the screw threads 48 and 46.

After these parts are assembled, although not shown in FIG. 3, an outer sleeve 144 is positioned about the elevator member 28 between the member 28 and the surface 136 of the ring lamp housing 120. The sleeve 144 is provided with a plurality of axially extending guide slots 146 so dimensioned and so positioned for passage therethrough of the shafts 140 of the roller bearing members 142 for preventing rotation of the ring lamp assembly 52 during vertical movement thereof. The sleeve 144 is keyed for fixedly positioning it relative to the housing member 24. As illustrated in FIG. 2, the sleeve 144 is provided with an inwardly extending peripheral flange 148 adjacent the bottom thereof for supporting the screw member 28. Next in succession, the collar member 78 is placed about the depending end of the cylindrical shell portion 26 of the housing member 24. A retaining ring 150 is threadably received within the open bottom end of the shell portion 26 to maintain the parts in assembled relation. At this point, the actuating rod 74 has the enlarged end thereof fitted within the keyhole slot 72 of the coupling member 68 with the threaded end 76 extending through a transverse slot 154 of the shell 26 and into the aperture 156 of the arm 80 (see FIG. 2) with the extender rod 82 being threadably secured thereto.

Referring now to FIGS. 1 and 2, the keratometer device 10 is then assembled to the microscope 12 and for this purpose, the upper end of the support member 24 is provided with rearwardly extending flange portions 160 for fitting on either side of the microscope mounting bracket 13, the flanges 160 having apertures 162 formed therein for passage therethrough of suitable fastening means such as a screw member 166. The keratometric device 10 is thus secured to the microscope 12. By reference specifically to FIG. 2, with the lamp housing 120 of the ring lamp assembly 52 in its uppermost solid line position, the prism assembly 50 will be in the position shown in solid line with the prisms 60 and 62 adjacent the objective lens 18. With the reference image provided by the ring lamp 126 being most distant from the corneal surface, the image reflected from the corneal surface will be at its smallest diameter for a given working distance.

For the principle of operation of a keratometric device in a binocular microscope, the aforementioned Terry U.S. Pat. No. 4,157,859 describes in detail the principles applicable to the utilization of a reference image in a fixed position relative to the binocular microscope system with the prisms likewise being in a fixed position relative thereto. Observation and measurement of the radius of curvature is determined in accordance with the zoom power of the microscope in one embodiment and the prism power in another.

In the instant invention, both the reference image generated by the ring lamp assembly 52 and the prism slide assembly 50 are movable and moved along the optical path of the binocular microscope 12. It is to be understood, however, that the reference image may be moved with the means for creating the additional images, that is the prisms 60 and 62, remaining stationary relative to the optical paths; or conversely the reference image may remain stationary while the prisms 60 and 62 of the prism slide assembly 50 may be moved relative to the optical path. However, the movement of either the ring lamp assembly 52 or the prism slide assembly 50 alone would require a much greater length of travel with the consequence of unduly extending into the available working distance of the surgeon. However, if the surgeon utilizes a larger working distance objective lens such as 200 mm or greater, individual movement of either the reference image or the means for splitting the images may be utilized.

By reference now to FIG. 4, there is an exaggerated side elevational view of the mounting of the prisms 60 and 62. Both of the prisms have the same prism power, that is the same wedge angle, this angle usually being rather small. For example, with a 150 mm working distance, a prism power of one to two diopters have been utilized. The prisms are mounted coaxially with the apexes aligned 90° relative to each other. A light passing upwardly through the prisms 60 and 62 will be deviated or bent in accordance with the angle of the wedge or prisms 60 and 62. In the peripheral region, that is the region where only wedge 60 transmits the light, the light will be deviated in a first direction. Where the light passes through both prisms as defined by the periphery of prism 62, the light will be bent at the same angle but in a different direction, this direction being 90° relative to the direction of bending of light passing through only the prism 60. This is in contrast to the prism positioning described in the aforementioned U.S. Pat. No. 4,157,859, in which individual prisms are aligned in a plane with each prism interrupting a portion of one or more of the optical paths.

Figure 5:
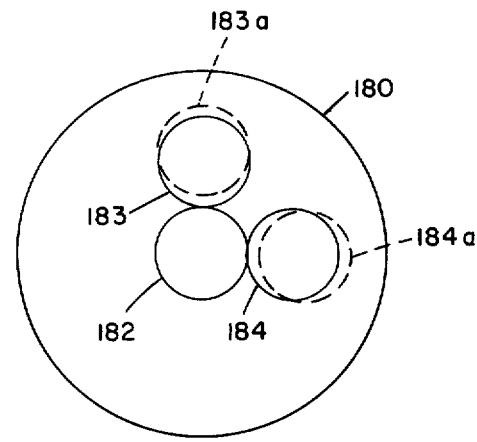
FIG. 5 is a diagramatic plan view depicting images formed on a spherical surface or object.

By reference to FIG. 5, there is shown diagramatically the surgical field of view 180 wherein, with a spherical surface, the surgeon views the three solid line circle images 182-184 with one of the images being formed by the ring lamp 126 and the other two images being formed by the optical deviations of the prism set consisting of prism 60 and 62. If the prism set 60 and 62 are moved while the ring lamp assembly 52 remained stationary, the result would be a moving apart of the centers of the so-formed images without a change in size of the viewed images. The central image 182 would remain stationary while the images 183 and 184 would move to the dotted line positions 183a and 184a without a change in size. With prism movement only, the keratometric device according to the invention could be calibrated to provide a radius of curvature measurement as determined by the distance of movement of the prism set 60 and 62 to a position where the surgeon views the three images in a predetermined relation such as tangential in accordance with the solid line depictions of images 182, 183 and 184 in FIG. 5. As the prism set 60 and 62 moves down the centers of the images comes closer together and conversely as the prism set 60 and 62 moves up toward the objective lens, the centers of the images move further apart, thus changing the image pattern.

Figure 6:
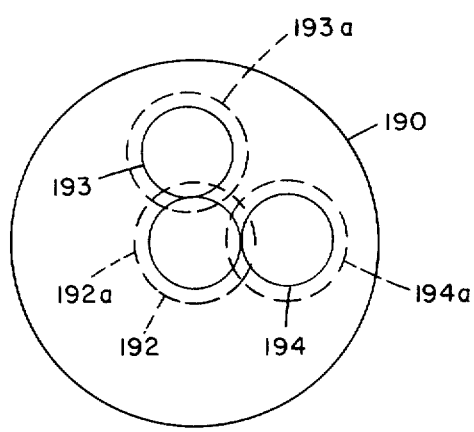
FIG. 6 is a plan diagramatic view similar to FIG. 5 depicting the changes in images under a different set of circumstances.

Conversely, by reference to FIG. 6, if the prism set 60 and 62 are to remain stationary relative to the objective lens 18, and the reference image, that is the image created by ring lamp 126 were to be moved relative to the optical path, the surgical field of view as depicted by circle 190 would include first, second and third aligned images 192-194 (shown in solid lines) when viewed through the microscope on a perfectly spherical surface, that is the images would be circular to form and would be in predetermined tangential relation for only one spherical surface or cornea of a given radius of curvature. As the reference image source approaches the surface, the centers of the circles or images viewed by the surgeon remain in the same position but the images so viewed get larger in diameter as depicted by the dotted line images 192a-194a inclusive. This movement of the ring lamp or reference image source only (with the prism assembly 60 and 62 remaining fixed) can likewise be calibrated to a radius of curvature in accordance with the ring lamp assembly 50 position.

In accordance with the embodiment shown and described, both the ring lamp assembly 52 and prism slide assembly 50 are moved in relative proportion to each other in the same direction at the same type by turning the knob 44, this producing a composite effect of the movement of the centers of the images viewable by the surgeon through the binocular eyepieces 20 and 22 as well as a changing of the diameter of the circles or images viewed by the surgeon. By movement of both the ring lamp assembly 52 and the prism slide assembly 50 in proportional unison, the length of the keratomertic device 10 depending below the objective lens 18 may be shortened thus conserving the maximum amount of usable working distance for the surgeon in the performance of the operation. By reference to FIG. 2 as the knob 44 is turned in a direction to lower the ring lamp 120 to the dotted line position 120a, (as depicted by the double ended arrows therebetween) the prism slide assembly 50 likewise moves downwardly to the dotted line position indicated by the reference numeral 50a.- During this downward travel, the keyhole slot 72 of the coupling member 68 enables the actuating rod 74 to remain stationary until the coupling member 68 moves to the lowermost position depicted in dotted lines and designated by reference numeral 68a. During this movement or at any intermediate time, the surgeon may position the prism assembly 60 and 62 out of the optical path by withdrawing on the knob 84 to the dotted line position designated 84a which then slides the prism tray 56 laterally until the prism tray 56 is in its rightmost position (as viewed in FIG. 2) as generally illustrated by the position of the coupling member 68 shown in dotted lines and designated 68b. This movement is also illustrated by the dotted line position of the prism assembly designated 60a and 62a, this movement corresponding to a withdrawing of the knob 84 with the prism assembly 50 in the solid line position shown in FIG. 2.

In order to enable the surgeon to determine the axis or meridian of the eye, the prism set 60 and 62 is rotatable or pivotal about the longitudinal axis of the optical paths of the microscope 12. This is illustrated in FIG. 1 wherein by grasping the handle 84 the surgeon may pivot the collar 78 to the right or to the left plus or minus 45° from a reference point, the reference point being enscribed, along with the angle degree markings as a protractor scale 121 on the external surface of the ring lamp housing 120, with the position being noted by virtue of the index pointer 88, the pointer 88 having a sufficient length to maintain alignment with the protractor scale 121 during vertical movement of the ring lamp assembly 52.

By reference to FIG. 3, for the purpose of providing an electrical signal indicative of the composite movement or position of the ring lamp assembly 52 and prism slide assembly 50, a potentiometer 200 is provided with a ring gear 202 in meshing engagement with the ring gear 34. This potentiometer 200 is suitably secured to the side of the housing member 24 and then suitably concealed within a control console cover 204 (see FIG. 1). The control console cover 204 may also include actuating switches 206 and 208 as well as a visual indicator 210, as desired. A digital display 212 is mounted on the microscope 14 at a position adjacent the binocular eyepieces 20 and 22 for enabling the surgeon to read the measured radius of curvatures at a convenient location.

Figure 7:
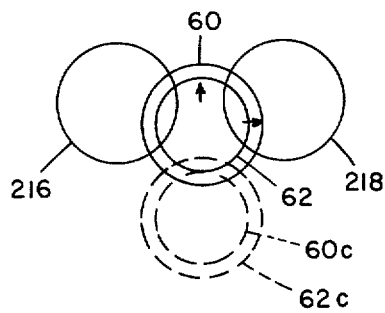
FIG. 7 is a diagramatic plan view illustrating the positioning of the prism set of FIG. 4 relative to the optical paths of the microscope.

FIG. 7 is a diagrammatical plan view in which the circles 216 and 218 depict the two optical paths corresponding to the optical path of each eyepiece 20 and 22 with the centrally disposed concentric circles illustrating the positioning of the prisms 60 and 62 relative to the optical paths 216 and 218. The dotted line concentric depictions designated 60c and 62c illustrate the position of the prism assembly with the prism tray 56 withdrawn. It is to be noted that the prism 60 and 62 do not entirely block the optical path 216 and 218, but instead simply intrude into both optical paths. With this positioning, each optical path 216 or 218 enables the viewing of all three images through each of the eyepieces 20 and 22. The arrows on the prism 62 and the periphery of the prism 60 displaced by 90° indicate the orientation of the prisms relative to each other for providing the images viewed by the surgeon as shown in FIGS. 5 and 6. The unobstructed portions of the optical paths 216 and 218 pass through to the eyepieces 20 and 22 the actual original reflection of the reference image created by the ring lamp 126. The prism 60 "clones" this image into a second image displaced at an angle determined by the apex orientation of the prism as well as the diopter power or wedge angle of the prism; similarly, the prism 62 (the combined power of both prisms 60 and 62) then "clones" or forms an additional image displaced 90° relative to the image formed by prism 60, this image forming of the prism set 60 and 62 generating two additional images viewable by the surgeon along with the original image. Thus, the prism set 60 and 62 optically forms two additional images which, in conjunction with the original image, are in a predetermined orientation relative to each other and with the corneal surface being spherical, and further with the prism slide assembly 50 and ring lamp assembly 52 in proper position relative to each other and to the optical path, the images viewed will have two of the images tangential to the third, this position providing an indication of the radius of curvature.

Figure 8:
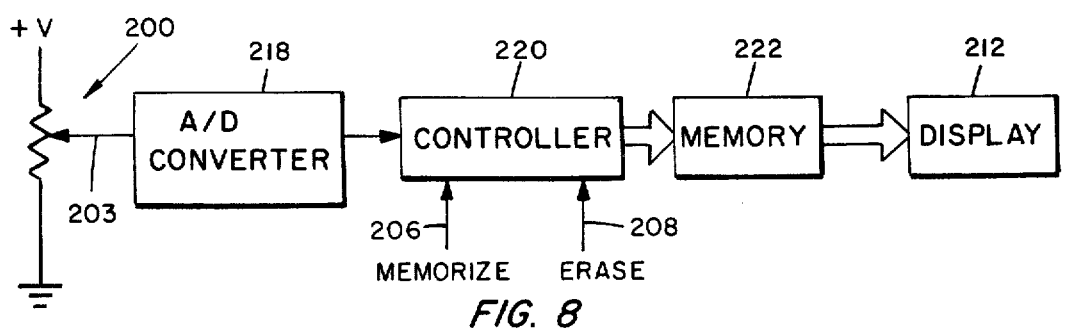
FIG. 8 is a functional block diagram of the circuitry in the device of FIG. 1.

By reference to FIG. 8, this position will be indicated by the physical position of the wiper 203 of the potentiometer 200 (shown in schematic form) which has the other ends thereof connected between a positive source of voltage and ground. The analog signal appearing on the wiper or lead 203 will be converted to a digital signal by an analog-to-digital converter 218, with this digital output being transferred to a controller 220. The controller 220 is provided with two inputs bearing reference numerals 206 and 208 to correspond to the actuating switches 206 and 208 on the control console 204. These inputs are designated "memorize" and "erase." These inputs provide the surgeon with the capability of memorizing a preoperative corneal radius of curvature measurement which the surgeon can return to postoperatively by a subsequent depression of the memorize switch 206. This stored value can be erased by the input 208. The controller 220 selects a portion of the memory 222 corresponding to the analog value determined and displays this value on the display 212. For calibration purposes, the memory 22 contains a lookup table of values of radius of curvature readings corresponding to analog inputs. Alternatively, the memory may contain an algorithm or computer program for calculating the corresponding value to be displayed. In either event, digital value is displayed at display 312 corresponding to the composite position of the ring lamp assembly 52 and prism slide assembly 50.

While there has been shown and described a preferred embodiment, it is to be understood that various other adaptations and modifications may be made within the spirit and scope of the invention. The elevator member 28 may be utilized with only one screw thread on either the exterior or the interior to move only one of the ring lamp 120 or prism slide assembly 50 as desired with the length of travel being correspondingly longer. In addition, rather than have the support member 24 stationary relative to the microscope body 14 with the prism assembly 60 and 62 being rotatable relative thereto, the converse may be utilized. That is, the prism assembly may be rendered non-pivotable (although slidable) with the support member 24 being pivotable relative to the optical axes of the optical paths 216 and 218. Additionally, to compensate for the intrusion of the depending parts of the keratometric device 10 into the working space, a suitable working distance adjusting lens may be placed over the open bottom end by affixing the corrective lens to the retainer ring 150, thus restoring the original working distance. It is, therefore, to be understood, that other modifications may be made within the spirit and scope of the invention.

What is claimed is:

1. In a keratometric device for measuring the radius of curvature of a spherical object and for use with a binocular microscope having objective lens means, the combination comprising:

support means attachable to the microscope body;

ring lamp means attached to said support means for projecting a reference image on said object;

prism means attached to said support means intermediate said object and said objective lens means, said prism means being positioned for extending partially into the optical path of said microscope for optically forming at least one other like image viewable with said reference image through said microscope; and elevator means for moving one of said ring lamp means and said prism means relative to said object for varying one of the size and the relative positions of the viewed images to a predetermined image pattern indicative of the radius of curvature of said object, said elevator means including a generally cylindrical member having first screw means coacting with said ring lamp means and second screw means coacting with said prism means for moving said prism means and said ring lamp means concurrently upon rotation of said cylindrical member.

2. The combination according to claim 1 wherein said prism means includes a first prism for deviating the reflected image in a first direction and a second prism for deviating the reflected image in a second mutually perpendicular direction.

3. The combination according to claim 2 wherein one of said prisms is mounted atop the other, and one of said prisms is of a smaller size.

4. The combination according to claim 3 wherein said prism means further includes a slidable tray member having said first and second prisms mounted thereon, said tray member being slidable radially for enabling movement of said prism means out of the optical path of said microscope.

5. The combination according to claim 4 wherein said prism means further include means for pivoting said first and second prisms.

6. The combination according to claim 1 further including means coupled to said means for moving for providing an electrical signal indicative of the radius of curvature.

7. The combination according to claim 6 further including electronic means responsive to said signal for generating a numerical display indicative of the value of the radius of curvature.

8. In a keratometric device for measuring the radius of curvature of a spherical object and for use with a binocular microscope having objective lens means, the combination comprising:
    a housing member configured for attachment to the microscope, said housing member having a cylindrical shell portion;
    a generally cylindrical elevator member configured for mounting about said shell portion for rotation relative thereto, said elevator member having a first screw thread on the exterior thereof and a second screw thread on the interior thereof;
    reference image projection means operatively coupled to said first screw thread;
    prism slide assembly means operatively coupled to said second thread, said prism slide assembly means including prism means in the optical path of said microscope;
    means coupled to said housing member for rotating said elevator member and moving said reference image projection means and said prism slide assembly means concurrently relative to the objective lens of said microscope.

9. The combination according to claim 8 wherein said prism slide assembly means further includes means for pivoting said prism means relative to the optical path of said microscope and means for moving said prism means out of the optical path of said microscope.

10. The combination according to claim 9 wherein said combination further includes a digital display, electronic circuit means, and means coupled to said elevator member for providing a visual display indicative of the positions of said prism slide assembly means and said reference image projection means.

11. The combination according to claim 10 wherein said means coupled to said elevator means includes a potentiometer and said electronic circuit means includes memory means for converting the signal from the potentiometer into a numerical value indicative of the radius of curvature of an object at a given working distance from the microscope.

12. In a keratometric device for use with a binocular microscope having objective lens means and for measuring the radius of curvature of a spherical object at a given distance along the axis of the optical path of the microscope, the combination comprising:
    support means attachable to the microscope body;
    lamp means attached to said support means for projecting a reference image on said object;
    prism means attached to said support means intermediate said object and said objective lens means, said prism means being positioned for extending partially into the optical path of said microscope for optically forming at least one other like image viewable with said reference image through said microscope; and
    means for moving one of said lamp means and said prism means in an axial direction relative to the said optical path and relative to said objective lens for varying one of the size and the relative positions of the viewed images to a predetermined image pattern indicative of the radius of curvature of said object.

13. The combination according to claim 12 wherein said prism means includes a first prism for deviating the reflected image in a first direction and a second prism for deviating the reflected image in a second mutually perpendicular direction.

14. The combination according to claim 13 wherein one of said prisms is mounted atop the other, and one of said prisms is of a smaller size.

15. The combination according to claim 14 wherein said prism means further includes a slidable tray member having said first and second prisms mounted thereon, said tray member being slidable radially for enabling movement of said prism means out of the optical path of said microscope.

16. The combination according to claim 12 wherein said means for moving includes elevator means for axially moving said lamp means and said prism means concurrently.

17. The combination according to claim 16 wherein said elevator means moves said lamp means and said prism means concurrently in the same direction in proportional relation.

* * * * *